(12) United States Patent
Park et al.

(10) Patent No.: US 9,676,739 B2
(45) Date of Patent: Jun. 13, 2017

(54) ACID DIANHYDRIDE, METHOD FOR PREPARING SAME, AND POLYIMIDE PREPARED THEREFROM

(71) Applicant: KOLON INDUSTRIES, INC., Gwacheon-si, Gyeonggi-do (KR)

(72) Inventors: Hyo Jun Park, Yongin-si (KR); Hak Gee Jung, Yongin-si (KR); Chang Sik Ha, Busan (KR); Prdip Kumar Tapaswi, Busan (KR); Young Sik Jeong, Ulsan (KR)

(73) Assignee: KOLON INDUSTRIES, INC., Gwacheon-si (KR)

(*) Notice: Subject to any disclaimer, the term of this patent is extended or adjusted under 35 U.S.C. 154(b) by 5 days.

(21) Appl. No.: 14/890,658

(22) PCT Filed: May 16, 2014

(86) PCT No.: PCT/KR2014/004394
§ 371 (c)(1),
(2) Date: Nov. 12, 2015

(87) PCT Pub. No.: WO2014/185739
PCT Pub. Date: Nov. 20, 2014

(65) Prior Publication Data
US 2016/0108014 A1    Apr. 21, 2016

(30) Foreign Application Priority Data

May 16, 2013    (KR) .................. 10-2013-0055392

(51) Int. Cl.
| | | |
|---|---|---|
| *C07D 307/60* | (2006.01) | |
| *C11D 3/33* | (2006.01) | |
| *C08G 73/02* | (2006.01) | |
| *C08G 73/10* | (2006.01) | |
| *C08L 79/08* | (2006.01) | |
| *C11D 3/37* | (2006.01) | |

(52) U.S. Cl.
CPC ....... *C07D 307/60* (2013.01); *C08G 73/0233* (2013.01); *C08G 73/0273* (2013.01); *C08G 73/1007* (2013.01); *C08G 73/1028* (2013.01); *C08G 73/1075* (2013.01); *C08L 79/08* (2013.01); *C11D 3/33* (2013.01); *C11D 3/3719* (2013.01)

(58) Field of Classification Search
CPC .... C11D 3/33; C11D 3/3719; C08G 73/1007; C07D 307/60
See application file for complete search history.

(56) References Cited

U.S. PATENT DOCUMENTS

| | | | | |
|---|---|---|---|---|
| 3,158,635 A | * | 11/1964 | Kezerian | .................. B03D 1/01 |
| | | | | 252/175 |
| 4,290,960 A | | 9/1981 | Ross et al. | |
| 4,454,310 A | | 6/1984 | Oka et al. | |
| 4,931,540 A | | 6/1990 | Mueller et al. | |
| 5,438,105 A | | 8/1995 | Nagata | |
| 5,466,867 A | * | 11/1995 | Lin | ....................... C07C 227/18 |
| | | | | 562/554 |
| 5,849,948 A | | 12/1998 | Patel et al. | |
| 7,005,165 B2 | | 2/2006 | Gibbons et al. | |

OTHER PUBLICATIONS

USPTO srtructure search, Jan. 2017.*
S. Vijay Kumar et al., "Structure-property relationships for partially aliphetic polyimides," Journal of Polymer Research, Sep. 2011, pp. 1111-1117, vol. 18, No. 5.
Danming Chao et al., "Synthesis of novel poly(amic acid) and polyimide with oligoaniline in the main chain and their thermal, electrochemical, and dielectric properties," Polymer, Mar. 17, 2010, pp. 4518-4524, vol. 51, No. 20.
Quantao Li et al., "Preparation of Poly(amic acid) and Polyimide via Microwave-Assisted Polycondensation of Aromatic Dianhydrides and Diamines," Macromolecular Symposia, Jan. 2008, pp. 148-156, vol. 261, No. 1.
International Searching Authority, International Search Report of PCT/KR2014/004394 dated Aug. 27, 2014.
Zhenhai Liu, "Thermal analysis of polyarylene ether sulfones and polyimides", Thermochimica Acta, 1991, vol. 183, pp. 73-90.
The State Intellectual Property Office of the Peoples Republic of China; Communication dated Dec. 1, 2016 in counterpart Chinese application No. 201480028547.0.

* cited by examiner

*Primary Examiner* — Gregory Listvoyb
(74) *Attorney, Agent, or Firm* — Sughrue Mion, PLLC

(57) ABSTRACT

The present invention relates to a novel acid dianhydride, a method for preparing the same, and a polyimide prepared therefrom. More specifically, the acid dianhydride according to the present invention is useful as a colorless transparent polyimide unit exhibiting excellent thermal stability and a low dielectric ratio, and the polyimide of the present invention has excellent solubility to an organic solvent compared with the conventional polyimide.

8 Claims, No Drawings

ACID DIANHYDRIDE, METHOD FOR PREPARING SAME, AND POLYIMIDE PREPARED THEREFROM

CROSS REFERENCE TO RELATED APPLICATIONS

This is a National Stage of International Application No. PCT/KR2014/004394 filed May 16, 2014, claiming priority based on Korean Patent Application No. 10-2013-0055392 filed May 16, 2013, the contents of all of which are incorporated herein by reference in their entirety.

TECHNICAL FIELD

The present invention relates to an acid dianhydride, a preparation method thereof, and a polyimide prepared therefrom.

BACKGROUND ART

Polyimide finds a wide spectrum of applications in the electronic material industry including protecting materials, insulation materials, color filters, etc. for liquid crystal displays and semiconductors by virtue of its high mechanical strength, thermal resistance, and solvent resistance. In addition, expectation has recently been made of the use of polyimide as a material for optical telecommunication and as a substrate for mobile phones.

With the recent advances in these industries, materials having advanced properties are increasingly demanded. For example, not only are mechanical properties such as thermal resistance and solvent resistance needed, but also functions according to uses, such as transparency, etc., are requested in polyimide for use in this field.

Appearing with a dark amber color, wholly aromatic polyimides for general purposes, which can be obtained by the polycondensation of aromatic tetracarboxylic dianhydride with aromatic diamine, cannot be applied where high transparency is needed. In addition, since wholly aromatic polyimide is insoluble in organic solvents, its precursor polyamic acid is, in practice, employed before film formation through thermal ring-closing dehydration.

One strategy for achieving transparency is known, wherein aliphatic tetracarboxylic dianhydride is polycondensed with aromatic diamine polyimide to give a polyimide precursor, followed by conversion into polyimide that is relatively colorless, and highly transparent (Japanese Patent Unexamined Application Publication Nos. Hei 2-24294 and Sho 58-208322).

However, the polyamic acids and polyimides that are based on unsubstituted aliphatic tetracarboxylic dianhydride are almost insoluble in general organic solvents, and soluble only in polar organic solvents with high boiling points. In this context, a high temperature is employed upon the formation of the film so as to remove the solvent, exerting undesirable effects on other organic materials of organic EL devices.

In recent years, a polyimide prepared from the monomer 1,2,3,4-cyclopentane tetracarboxylic dianhydride (hereinafter referred to as "CPDA") has been suggested for use as a gas barrier film of organic electroluminescence (hereinafter referred to as "organic EL") (Japanese Patent Unexamined Application Publication No. 2006-232960).

However, this polyimide needs to be improved in thermal resistance and is not of sufficient solubility in organic solvents in addition to having a low degree of polymerization.

DISCLOSURE

Technical Problem

It is a primary object of the present invention to provide a novel acid dianhydride as a material monomer for a polyimide that has a low dielectric constant and exhibits excellent thermal stability, solubility in organic solvents, and light transmittance while retaining the properties of polyimide itself, and a method for preparing the same.

It is another object of the present invention to provide a polyamic acid containing the novel acid dianhydride, and a polyimide prepared through the ring-closing dehydration of the polyamic acid.

Technical Solution

According to one aspect for accomplishing the above object, the present invention provides an acid dianhydride represented by the following Chemical Formula 1:

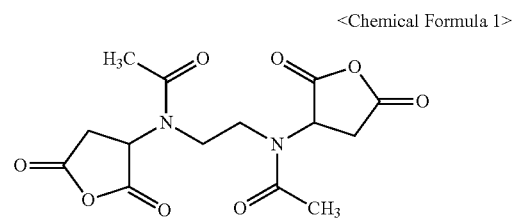 [SMILES: CC(=O)N(CCN(C(C)=O)C1CC(=O)OC1=O)C1CC(=O)OC1=O]

<Chemical Formula 1>

In accordance with another aspect thereof, the present invention provides a method for preparing an acid dianhydride, represented by the following Chemical Formula 1, comprising:

(a) subjecting a compound represented by the following Chemical Formula 2 to N-alkylation in the presence of a base catalyst to give a compound represented by the following Chemical Formula 3; and (b) converting the compound of Chemical Formula 3 into the compound of Chemical Formula 1 by ring-closing dehydration in the presence of a dehydrating agent:

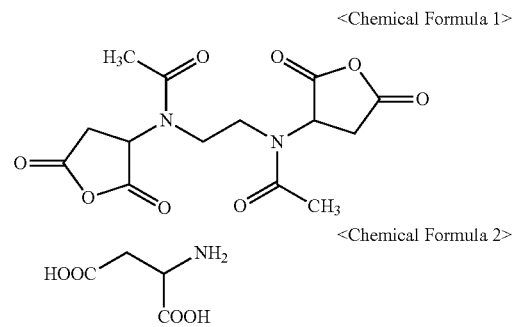

<Chemical Formula 1>

<Chemical Formula 2>

-continued

<Chemical Formula 3>

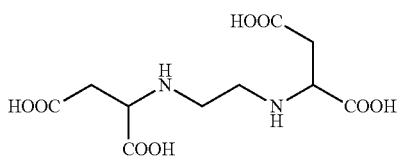

In one preferred embodiment of the present invention, the base catalyst of step (a) is selected from the group consisting of potassium hydroxide, sodium hydroxide, barium hydroxide, calcium hydroxide, aluminum hydroxide, magnesium hydroxide, and a combination thereof.

In another preferred embodiment of the present invention, the ring-closing dehydration of step (b) is conducted at 40~100° C. for 4~28 hrs.

In another preferred embodiment of the present invention, the dehydrating agent of step (b) is used in an amount of 2~10 moles per mole of the compound of Chemical Formula 3.

In another preferred embodiment of the present invention, the dehydrating agent of step (b) is selected from the group consisting of acetic anhydride, pyridine, isoquinoline, a tertiary amine, and a combination thereof.

A further aspect of the present invention provides a polyamic acid, prepared by reacting an acid dianhydride represented by the following Chemical Formula 1 with diamine:

<Chemical Formula 1>

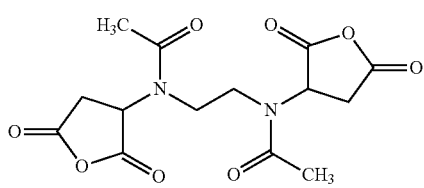

A still further aspect of the present invention provides a polyimide, prepared from the polyamic acid of claim 7 by ring-closing dehydration.

Advantageous Effects

Provided according to the present invention are a novel acid dianhydride useful for the preparation of a colorless transparent polyimide that exhibits excellent thermal stability and has a low dielectric constant while retaining excellent properties of polyimide itself, and a method for preparing the same.

Exhibiting excellent thermal stability and having a low dielectric constant, the colorless transparent polyimide of the present invention finds applications in a variety of material industries including protecting and insulating materials in liquid crystal display devices or semiconductors, and materials for optical communication such as optical waveguides

MODE FOR INVENTION

Unless otherwise defined, all terms used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

In accordance with an aspect thereof, the present invention addresses an acid dianhydride represented by the following Chemical Formula 1:

<Chemical Formula 1>

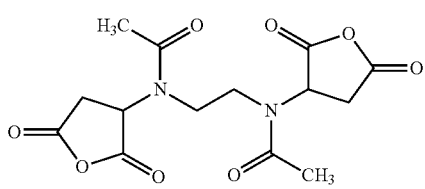

In accordance with another aspect thereof, the present invention addresses a method for preparing an acid dianhydride, represented by the following Chemical Formula 1, comprising: (a) subjecting a compound represented by the following Chemical Formula 2 to N-alkylation in the presence of a base catalyst to give a compound represented by the following Chemical Formula 3; and (b) converting the compound of Chemical Formula 3 into the compound of Chemical Formula 1 by ring-closing dehydration in the presence of a dehydrating agent:

<Chemical Formula 1>

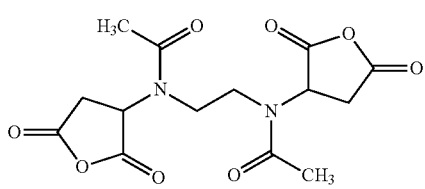

<Chemical Formula 2>

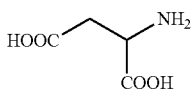

<Chemical Formula 3>

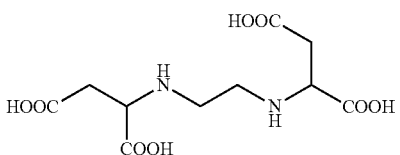

As a rule, aliphatic polyimide exhibits higher transparency and is lower in dielectric constant, compared to aromatic polyimide, because of its low intramolecular density, polarity, and low inter- or intramolecular charge transfer. Thanks to these properties, aliphatic polyimide has attracted much attention for use as interlayer insulating materials in optoelectronics.

For use in preparing an aliphatic polyimide that is of high transparency and low dielectric constant, N-acetylated-1,2-ethylenediamine-disuccinic anhydride (an acid dianhydride represented by Chemical Formula 1) is synthesized in the present invention.

Since the acid dianhydride represented by Chemical Formula 1 in accordance with the present invention contains at least one intramolecular nitrogen atom, the lone electron pair on the nitrogen atom causes intra- or intermolecular interaction. In this mechanism, the polyamide of the present invention can be greatly improved in solubility and mechanical strength while retaining its excellent intrinsic properties.

The acid dianhydride according to the present invention may be prepared simply using a two-step method including alkylation and ring-closing dehydration.

Briefly, the acid dianhydride according to the present invention is prepared by N-alkylating a compound represented by Chemical Formula 2 to give a compound represented by Chemical Formula 3, and subjecting the compound of Chemical Formula 3 to ring-closing dehydration in the presence of a dehydrating agent.

This process is summarized as illustrated in the following Reaction Scheme 1.

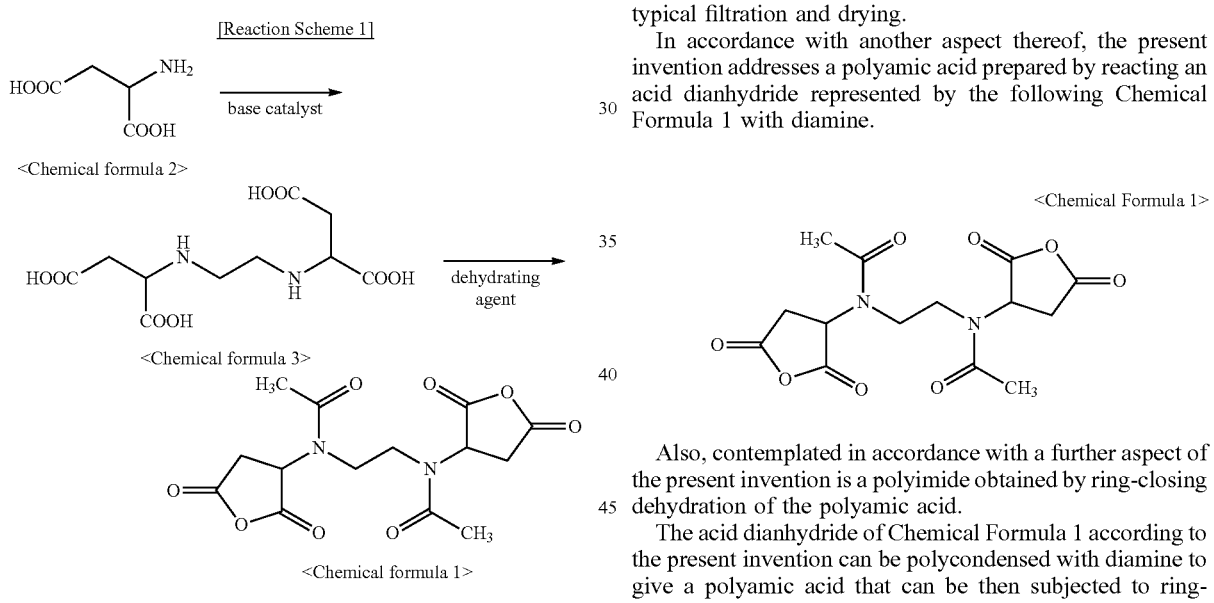

First, as illustrated in Reaction Scheme, a compound (L-aspartic acid) represented by Chemical Formula 2 is N-alkylated into a compound represented by Chemical Formula 3 in the presence of a base catalyst.

The base catalyst useful for the N-alkylation reaction may be selected from the group consisting of potassium hydroxide, sodium hydroxide, barium hydroxide, calcium hydroxide, magnesium hydroxide, and a combination thereof in view of cost and ease of handling. However, the base catalyst may be freely selected according to ion transfer and exchange rates.

In the present invention, the reaction substrate itself is preferably used as a solvent, but a separate solvent may be employed. No particular limitations are imposed on the reaction solvent if it does not interrupt the reaction. For example, 1,4-dioxane, toluene, NMP (N-Methyl-2-pyrrolidone), DMAc (dimethylacetamide), or 1,2-dibromoethane may be used.

The compound of Chemical Formula 3 is ring closed by dehydration in the presence of a dehydrating agent to afford the aliphatic acid dianhydride represented by Chemical Formula 1. The ring-closing dehydration is conducted at 40~100° C. for 4~28 hrs. At higher than 100° C. or for longer than 28 hrs, the catalyst or the solvent is prone to evaporating, thus decreasing the yield. At lower than 40° C., the reaction should be conducted for a prolonged time, or within 4 hrs, the reaction does not proceed sufficiently, decreasing the yield.

The dehydrating agent may be at least one selected from the group consisting of acetic anhydride, and a tertiary amine such as pyridine, isoquinoline and triethylamine. In terms of efficiency, acetic anhydride and/or pyridine is preferred.

Based on 1 mole of the compound of Chemical Formula 3, the dehydrating agent may be used in an amount of 2 or more moles, and preferably in an amount of 2 to 10 moles. When the amount of the dehydrating agent is less than 2 moles per mole of the compound of Chemical Formula 3, the reaction does not proceed sufficiently with the resultant decrease of the yield. More than 10 moles of the dehydrating agent is disadvantageous in view of cost.

After completion of the above-mentioned reactions, the acid dianhydride of Chemical Formula 1 is obtained by typical filtration and drying.

In accordance with another aspect thereof, the present invention addresses a polyamic acid prepared by reacting an acid dianhydride represented by the following Chemical Formula 1 with diamine.

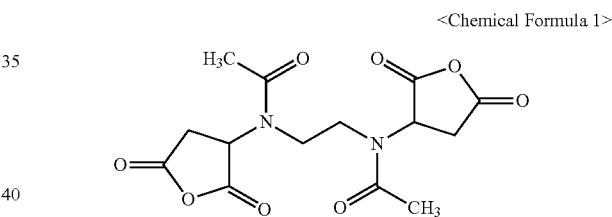

Also, contemplated in accordance with a further aspect of the present invention is a polyimide obtained by ring-closing dehydration of the polyamic acid.

The acid dianhydride of Chemical Formula 1 according to the present invention can be polycondensed with diamine to give a polyamic acid that can be then subjected to ring-closing dehydration under heat or in the presence of a catalyst to afford a polyimide.

Without being particularly limited, the diamine may be one of various diamines typically used in the synthesis of polyimide. Concrete examples of the diamine include: aromatic diamines, such as p-phenylene diamine, m-phenylene diamine, 2,5-diaminotoluene, 2,6-diaminotoluene, 1,3-bis(4,4'-aminophenoxy)benzene, 4,4'-diamino-1,5-phenoxypentane, 4,4'-diaminobiphenyl, 3,3'-dimethyl-4,4'-diaminobiphenyl, 3,3'-dimethoxy-4,4'-diaminobiphenyl, 4,4'-diaminodiphenylether, 4,4'-diaminodiphenylmethane, 2,2'-diaminodiphenylpropane, bis(3,5-diethyl-4-aminophenyl)methane, diaminodiphenylsulfone, diaminobenzophenone, diaminonaphthalene, 1,4-bis(4-aminophenoxy)benzene, 1,4-bis(4-aminophenyl)benzene, 9,10-bis(4-aminophenyl)anthracene, 1,3-bis(4-aminophenoxy)benzene, 4,4'-bis(4-aminophenoxy)diphenylsulfone, 2,2-bis[4-(4-aminophenoxy)phenyl]propane, and 2,2'-trifluoromethyl-4,4'-diaminobiphenyl; cyclic diamines, such as 1,4- diaminocyclohexane, 1,4-cyclohexane bis(methylamine), and 4,4'-diaminodicyclohexyl methane; and aliphatic diamines, such as tetramethylene diamine, and hexamethylene diamine. These diamines may be used solely or in combination.

No particular limitations are imposed on the preparation of the polyamic acid of the present invention. It may be achieved by reacting and polymerizing the acid dianhydride of Chemical Formula 1 with diamine in a typical process. For convenience, an aliphatic dianhydride represented by Chemical Formula 1 and diamine may be mixed and reacted in an organic solvent.

Examples of the organic solvent include m-cresol, N-methyl-2-pyrrolidone (NMP), N,N-dimethyl formamide (DMF), N,N-dimethyl acetamide (DMAc), N-methyl caprolactam, dimethyl sulfoxide (DMSO), tetramethyl urea, pyridine, dimethylsulfone, hexamethyl phosphoramide, and γ-butyrolactone. These solvents may be used solely or in combination. Unable as it is to dissolve polyamic acid, an additional solvent may be used in addition to the solvent if it allows for the formation of a uniform solution.

The solution polymerization may be conducted at −20~150° C., and preferably at −5~100° C. In addition, the molecular weight of the polyamic acid may be controlled by adjusting the molar ratio of the acid dianhydride of Chemical Formula 1 to the diamine. A molar ratio nearer to 1 results in a higher molecular weight of the produced polyamic acid.

The polyimide of the present invention is obtained from the polyamic acid prepared above through ring-closing dehydration. Here, a conversion rate of polyimide from polyamic acid (ring-closing dehydration rate) is defined as a imidization rate. The rate of imidization for the polyimide of the present invention is not limited to 100%, and may be given a value of 1~100%, as needed.

Without being particularly limited, the ring-closing dehydration of polyamic acid may be achieved typically by heating or chemically with a known ring-closing dehydration catalyst. The ring-closing dehydration by heating may be conducted at 100~300° C., and preferably at 120~250° C.

As for the chemical method, its ring-closing dehydration may be conducted in the presence of a catalyst such as an organic base such as pyridine or triethyl amine, or an acetic anhydride. In this regard, the reaction temperature may be at −20~200° C. In this reaction, the polymerization solution of polyamic acid may be used as it is or after it is diluted. Alternatively, the polyamic acid may be dissolved in a suitable organic solvent after being recovered from the polymerization solution as described later. The organic solvent may be the same as is used for the polymerization of polyamic acid.

The polyimide (containing) solution thus obtained may be used as it is or may be added with methanol or ethanol to precipitate the polymer. This polymer may be isolated as a powder or may be re-dissolved in a suitable solvent. Any solvent can be used without limitations if it can dissolve the polymer. Selection for the solvent may be made from among, for example, m-cresol, 2-pyrrolidone, NMP, N-ethyl-2-pyrrolidone, N-vinyl-2-pyrrolidone, DMAc, DMF (dimethylformamide), and γ-butyrolactone.

A better understanding of the present invention may be obtained through the following examples that are set forth to illustrate, but are not to be construed as limiting the present invention.

EXAMPLE 1

1-1: Synthesis of Compound of Chemical Formula 3

In 1-L three-neck flask, 50.73 g (0.38 moles) of the compound (L-aspartic acid) of Chemical Formula 2 was mixed with 30 ml (50% aqueous solution) of potassium hydroxide, 13.94 g (0.19 mol) of potassium hydroxide, and 70 ml of distilled water. The flask was equipped with a condenser, an isobaric dropping funnel, a reflux condenser, and a magnetic stirrer. After 28 ml (50% aqueous solution) of 1,2-dibromoethane was carefully added through the third neck of the flask, the mixture was heated at 60° C. Potassium hydroxide (24 ml, 50% aqueous solution) was dropwise added to the mixture over 6 hrs under reflux. After completion of the reflux, water was introduced into the flask, and the solution was refluxed for an additional one hour. Then, the reflux was cooled over 1 hr while stirring, and then acidified into a pH of 3 with conc. HCl to form a white precipitate. The white precipitate was filtered, added with distilled water (225 ml), and adjusted to a pH of 11 with sodium hydroxide (50% aqueous solution). The pH was re-adjusted from 11 to 3.5 with HCl to form a precipitate that was then washed with water and dried at 65° C. in a vacuum. (17.9 g, yield 30%). The compound of Chemical Formula 2 was prepared as previously reported by Neal J. A., (Neal J. A., Rose N. J., *Inorg Chem*, 1968, 7, 2408).

The compound of Chemical Formula 3 thus obtained was measured for melting point (Buchi, M-560), and analyzed by NMR ($^1$H and $^{13}$C) (JEOL, JNM-LA400) and IR (AVATAR, 360 FT-IR).

m. p.: 215-217° C. (H$_2$O+MeOH)

$^1$H NMR (400 MHz, D$_2$O/KOH) δ 2.38-2.50 (m, 2H, CH$_2$CO$_2$), 2.62-2.67 (m, 2H, CH$_2$CO$_2$), 2.91-3.01 (m, 4H, CH$_2$CH$_2$), 3.55-3.58 (m, 2H, CH), (NH and CO$_2$H not observed at this pH); Anal. Calcd. for C$_{10}$H$_{16}$N$_2$O$_8$; C, 41.10; H, 5.52; N, 9.59%. Found: C, 40.97; H, 5.60; N, 9.64%; IR (KBr, cm$^{-1}$): 3530 (νO—H), 3422 (νN—H), 3044, 2807, 1723 (νC=O).

1-2: Synthesis of Acid Dianhydride of Chemical Formula 1

In a 50 ml flask equipped with a magnetic stirrer, 4.96 g (17 mmol) of the compound of Chemical Formula 3 obtained in Example 1-1, 3.18 g (35.7 mmol) of pyridine, and 3.6 g (35.7 mmol) of acetic anhydride were placed, and allowed to react at 60° C. for 24 hrs. After completion of the reaction, the reaction mixture was cooled and filtered. The filtrate was washed with 200 ml of acetic anhydride and 200 ml of purified diethylether, and dried at 40° C. in a vacuum oven. Recrystallization in 100 ml of acetic anhydride produced the compound of Chemical Formula 1. 2.48 g (yield 50%).

The compound of Chemical Formula 1 obtained was measured for melting point (Buchi, M-560), and analyzed by NMR CH and $^{13}$C) (JEOL, JNM-LA400) and IR (AVATAR, 360 FT-IR).

m.p.: 248-250° C. (Ac$_2$O)

$^1$H NMR (400 MHz, d6-DMSO) δ 2.01 (s, 3H, —NCOCH$_3$), 2.12 (s, 3H, —NCOCH$_3$), 2.83-2.91 (m, 2H, CH$_2$CO$_2$), 3.30 (dd, 2H, overlapped signals, CH$_2$CO$_2$), 3.65 (bd, 4H, CH$_2$CH$_2$), 4.66-4.60 (m, 2H, CH); $^{13}$C NMR (100 MHz, d6-DMSO): δ 173.8 (—NCOCH$_3$), 173.4 (COOCO), 172.9 (COOCO), 59.7 (α-CH), 51.2 (N—CH$_2$CH$_2$), 51.0 (N—CH$_2$CH$_2$), 37.1 (β-CH$_2$), 23.3 (—NCOCH$_3$); Anal.

Calcd. for $C_{14}H_{16}N_2O_8$; C, 49.41; H, 4.74; N, 8.23%. Found: C, 49.32; H, 4.80; N, 8.26%; IR (KBr, cm$^{-1}$): 2955, 1869, 1790 (vC=O), 1222, 1196, 1075 (C—O—C).

Although the preferred embodiment(s) of the present invention have(has) been disclosed for illustrative purposes, those skilled in the art will appreciate that various modifications, additions and substitutions are possible, without departing from the scope and spirit of the invention as disclosed in the accompanying claims.

The invention claimed is:

1. An acid dianhydride, represented by the following Chemical Formula 1:

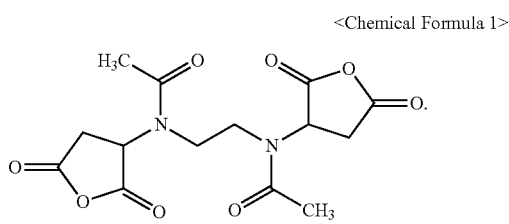 [SMILES: CC(=O)N(CCN(C(C)=O)C1CC(=O)OC1=O)C1CC(=O)OC1=O]

<Chemical Formula 1>

2. A method for preparing an acid dianhydride, represented by the following Chemical Formula 1, comprising:
   (a) subjecting a compound represented by the following Chemical Formula 2 to N-alkylation in the presence of a base catalyst to give a compound represented by the following Chemical Formula 3; and
   (b) converting the compound of Chemical Formula 3 into the compound of Chemical Formula 1 by ring-closing dehydration in the presence of a dehydrating agent:

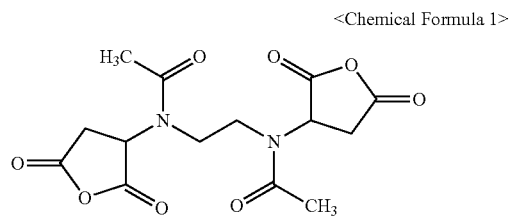 [SMILES: CC(=O)N(CCN(C(C)=O)C1CC(=O)OC1=O)C1CC(=O)OC1=O]

<Chemical Formula 1>

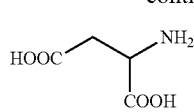

<Chemical Formula 2>

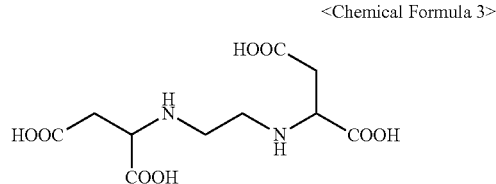

<Chemical Formula 3>

3. The method of claim 2, wherein the base catalyst of step (a) is selected from the group consisting of potassium hydroxide, sodium hydroxide, barium hydroxide, calcium hydroxide, aluminum hydroxide, magnesium hydroxide, and a combination thereof.

4. The method of claim 2, wherein the ring-closing dehydration of step (b) is conducted at 40~100° C. for 4~28 hrs.

5. The method of claim 2, wherein the dehydrating agent of step (b) is used in an amount of 2~10 moles per mole of the compound of Chemical Formula 3.

6. The method of claim 2, wherein the dehydrating agent of step (b) is selected from the group consisting of acetic anhydride, pyridine, isoquinoline, a tertiary amine, and a combination thereof.

7. A polyamic acid, prepared by reacting an acid dianhydride represented by the following Chemical Formula 1 with diamine:

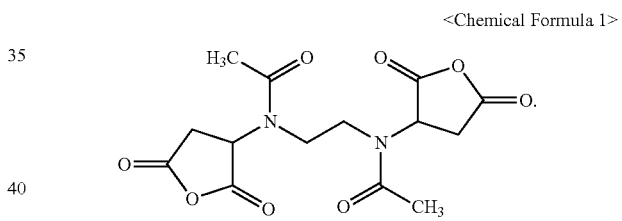

<Chemical Formula 1>

8. A polyimide, prepared from the polyamic acid of claim 7 by ring-closing dehydration.

* * * * *